United States Patent [19]

Neer et al.

[11] Patent Number: 5,300,031
[45] Date of Patent: Apr. 5, 1994

[54] APPARATUS FOR INJECTING FLUID INTO ANIMALS AND DISPOSABLE FRONT LOADABLE SYRINGE THEREFOR

[75] Inventors: Charles Neer, Milford; Frank M. Fago, Mason, both of Ohio; Paul E. Dieterlen, Covington, Ky.; James H. Goethel, Cincinnati, Ohio

[73] Assignee: Liebel-Flarsheim Company, Cincinnati, Ohio

[21] Appl. No.: 712,110

[22] Filed: Jun. 7, 1991

[51] Int. Cl.$^5$ .......................................... A61M 37/00
[52] U.S. Cl. ................... 604/154; 604/218; 604/232; 128/DIG. 1; 128/655
[58] Field of Search ............... 604/154, 228, 187, 218, 604/232, 131, 154, 155; 128/655, DIG. 1, 654

[56] References Cited

U.S. PATENT DOCUMENTS

| | | | |
|---|---|---|---|
| 1,988,480 | 1/1935 | Campkin | 604/155 X |
| 2,627,270 | 2/1953 | Glass | 604/155 |
| 3,348,545 | 10/1967 | Sarnoff et al. | |
| 3,631,847 | 1/1972 | Hobbs | 604/155 X |
| 3,701,345 | 10/1972 | Hellman et al. | |
| 3,752,145 | 8/1973 | Runnells et al. | 128/655 |
| 3,812,843 | 5/1974 | Wootten et al. | |
| 3,880,138 | 4/1975 | Wootten et al. | |
| 4,006,736 | 2/1977 | Kranys et al. | 128/655 |
| 4,150,672 | 4/1979 | Whitney et al. | |
| 4,267,836 | 5/1981 | Whitney et al. | 604/154 X |
| 4,636,198 | 1/1987 | Stade | |
| 4,677,980 | 7/1987 | Reilly et al. | 128/655 |
| 4,695,271 | 9/1987 | Goethel | |
| 4,869,720 | 9/1989 | Chernack | 604/228 |
| 5,002,538 | 3/1991 | Johnson | |
| 5,007,904 | 4/1991 | Densmore | 604/228 |

FOREIGN PATENT DOCUMENTS

| | | |
|---|---|---|
| 143895 | 8/1984 | European Pat. Off. |
| 346950 | 6/1985 | European Pat. Off. |
| 362484 | 7/1989 | European Pat. Off. |

Primary Examiner—C. Fred Rosenbaum
Assistant Examiner—Mark O. Polutta
Attorney, Agent, or Firm—Donald F. Frei; Joseph R. Jordan

[57] ABSTRACT

An animal fluid injector, replaceable syringe and method of replacement of the syringe in the injector are provided in which the syringe is loadable and unloadable into and from the injector through the open front end of a pressure jacket of the injector, thereby permitting replacement without retraction of the syringe plunger drive or disconnection of the injection tubing. The syringe is provided with a pressure restraining front end, such as an integral or removable cap with structure such as threads that lock the syringe to the front end of the jacket by mating with threads on the jacket. A mechanism in the injector, which includes, for example, a key on cam ring operated by a lever with one hand of an operator, interacts with structure such asymmetrically spaced notches on the back end of the syringe to, for example, rotate the syringe and simultaneously translate or rotate a coupling on the syringe plunger into and out of engagement with the plunger drive in the injector.

28 Claims, 11 Drawing Sheets

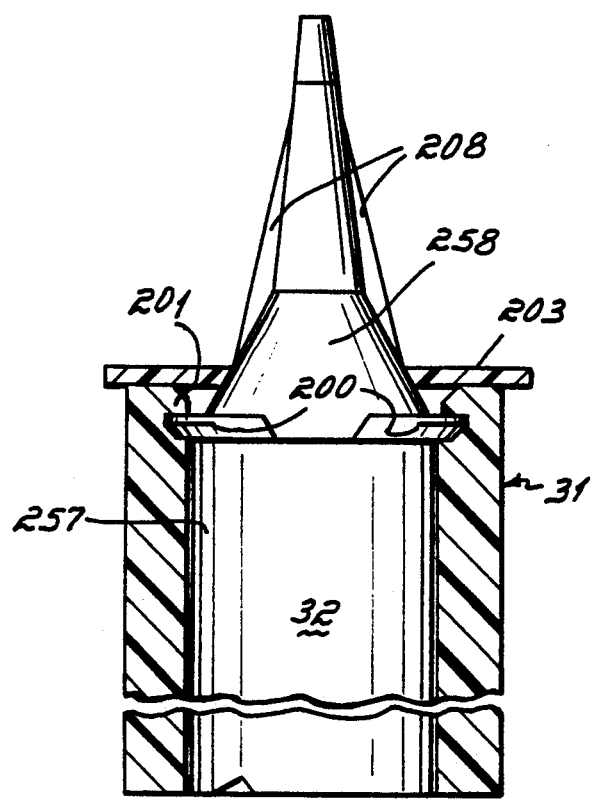
FIG. 15
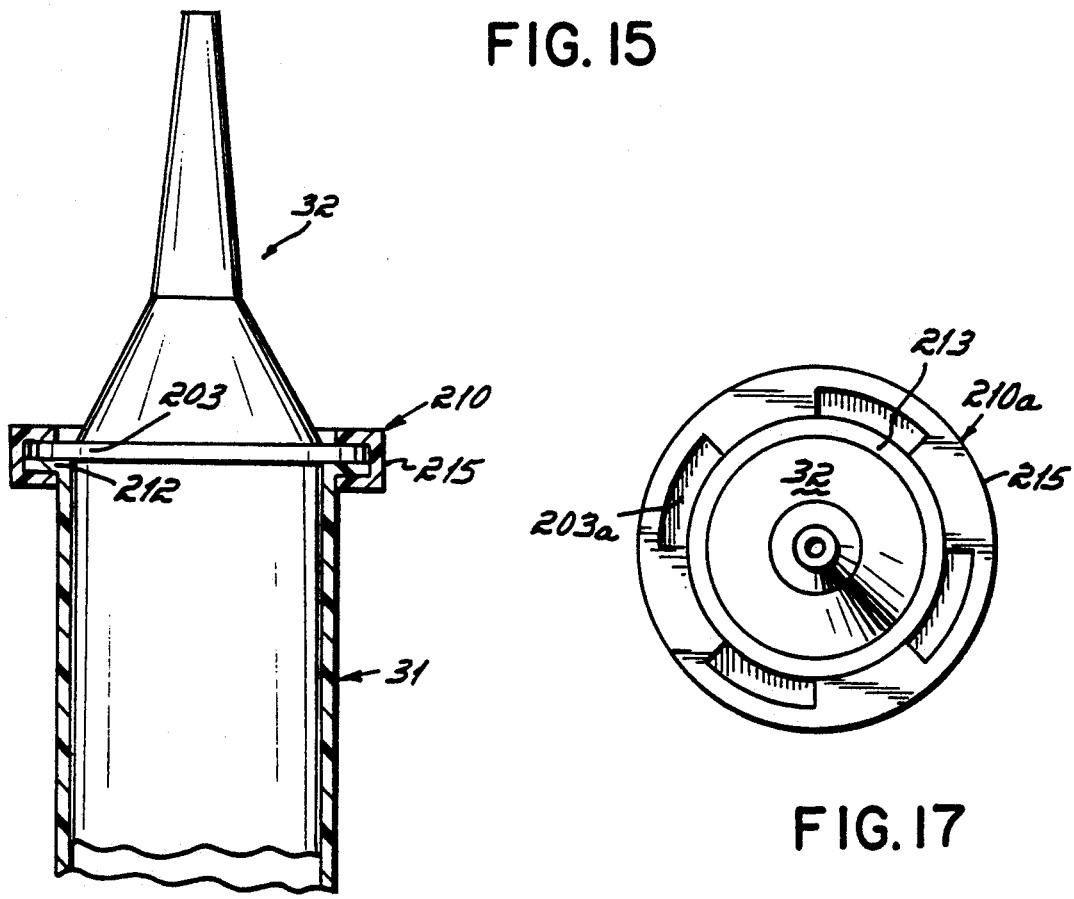
FIG. 16
FIG. 17

APPARATUS FOR INJECTING FLUID INTO ANIMALS AND DISPOSABLE FRONT LOADABLE SYRINGE THEREFOR

The present invention relates to injectors and more particularly to disposable replacement syringes for animal fluid injectors.

BACKGROUND OF THE INVENTION

Injectors are devices that expel fluid, such as contrasting media, from a syringe and through a tube into an animal. The injectors are provided with an injector unit, usually adjustably fixed to a stand or support, having a drive that couples to the plunger of the syringe to drive it forward to expel fluid into the tube, or that may be driven rearward to draw fluid into the syringe to fill it. Usually the syringe is a disposable replacement type.

In the injection phase where the plunger is driven forward, pressures are developed in the syringe that range from, for example, twenty-five psi for some applications to over 1000 to 1200 psi for other applications. Syringes that will contain fluid under such pressures are expensive and therefore impractical where the syringes are to be disposable. Accordingly, many such injectors, such as angiographic injectors, for example, have been provided with pressure jackets fixed to the injector units and into which the syringes are inserted. The pressure jackets contact the outer surfaces of the syringe to restrain the walls of the syringe against the internal pressures.

To hold the syringes in the pressure jackets, the jackets of the prior art have been configured to surround the front ends of the syringes to restrain the syringe front wall against forward acting forces of the drive and the fluid pressure and to hold the syringe in the jacket. Because the front end of the pressure jacket is closed, rear loading was necessary, and accessibility thereto was provided by hinging or rotating the jacket to allow for removal and replacement of the syringe from the rear. The opening and reclosing of the injector unit to replace the syringe requires a certain amount of time, which, in the course of the procedure being performed, is not wholly desirable.

Furthermore, while for many years injector units of various types have been capable of disconnection of the plunger drive from the drive coupling on the syringe plunger at any position of the plunger within the syringe, retraction of the drive is typically required before the syringe can be removed. This is because the opening of the injector unit to remove and insert the syringe from the rear requires, for example, a translating or rotating of the jacket from the axis of the drive, which cannot be achieved if the plunger drive is extended.

For example, at the end of an injection procedure, the syringe plunger typically is forward, as is the plunger drive. Since, in the prior art injectors that load from the rear, the pressure jacket is moved through the position that the drive occupies when extended in order to remove the syringe. Hence, the syringe cannot be immediately removed without retracting the plunger drive. Further, the disposable tubing that connects to the nozzle of the syringe must be disconnected from the syringe in order to remove the syringe from the jacket. Additionally, when an empty new syringe is inserted, the drive must be in its retracted position.

More often than not, the syringe is inserted empty and filled by retraction of the plunger with an injection tube connected to a supply of the fluid that is to be injected. In addition, before an empty new syringe can be filled, it is necessary that the plunger be fully forward in the syringe so that the syringe can be filled by rearward retraction of the plunger. As a consequence of the need with such prior art injectors to retract the drive upon loading the syringe, it is then necessary to fully advance the drive to the position in which it in engagement with the plunger and the plunger is in its full forward position. The drive then engages a coupling on the plunger of the replacement syringe. This need to retract and advance the drive contributes to a loss of time in the syringe replacement process.

Accordingly, there has been a need to more quickly load and unload disposable replacement syringes in angiographic injectors, and for injectors and replacement syringes that can accommodate a more efficient process of syringe replacement.

SUMMARY OF THE INVENTION

It is an objective of the present invention to provide a method and apparatus by which replaceable syringes can be more efficiently loaded into and unloaded from injectors.

It is a more particular objective of the present invention to provide an injector, more particularly an angiographic injector, a replacement syringe therefor, and a method of replacing the syringe in the injector that provide for more efficient replacement of the syringes in the injector. It is an additional objective of the present invention to provide an injector wherein a used syringe can be removed and a new one inserted in the injector without retraction of the drive from the pressure jacket, in most applications. It is a further objective of the invention to allow for the removal of the used syringe from the jacket without disconnection of the injector tube from the syringe nozzle.

It is still a further objective of the present invention to provide an injector, replaceable syringe and method of syringe replacement with which the replacement of the syringe can be achieved with simple motions by the operator or with rapid operation of injector unit mechanisms.

An additional objective of the present invention is to provide an injector and replaceable syringe therefor that will facilitate control of the orientation of the syringe in the jacket, and thereby provide for positive, rapid and reliable engagement of the syringe with locking structure that holds the syringe in the jacket, engagement of the plunger drive and plunger drive coupling, or connection of the injection tube to the outlet of the syringe.

A further objective of the present invention is to provide for easy to operate mechanism and reliable locking structure for locking the syringe in place in the pressure jacket of the injection unit.

Another objective of the present invention is to provide an injector and syringe arrangement that minimizes or eliminates the probability of spillage from the syringe nozzle flowing into the injector equipment, and otherwise enhancing the ability to maintain sterility and cleanliness 10 of the equipment.

According to the principles of the present invention, there is provided an angiographic injector having a front end loadable syringe that can be loaded into and removed from the injector pressure jacket through an opening that is provided in the front end of the pressure jacket. To provide this front end loadable feature, the syringes of the preferred and illustrated embodiments of the present invention are provided with a front wall that is pressure restraining, that is, is of sufficient strength to support the front of the syringe against the expected pressures within the syringe, and that is securable to the front end of the pressure jacket so as to complete the pressure restraining enclosure of the syringe within the pressure jacket and hold the syringe in the jacket. In one preferred form, this front end of the injector is formed of a separate pressure restraining cap made of material that is separate from the front wall of the syringe and may be reusable. In another preferred form, the cap may be formed integrally of the front syringe wall. With the cooperating structure of the jacket and the syringe, restraining of the pressure jacket along the front and sides of the syringe is provided where the jacket allows for the replacement of the syringe from the front.

In one preferred and illustrated embodiment of the invention, the front end of the syringe locks to the front end of the pressure jacket through a cooperating engagement of mating threads on the syringe jacket. The threads include external thread sections formed at the front end of the pressure jacket and internal threads formed on an outwardly extending flange or rim of the front wall of the syringe, preferable on a pressure restraining cap. Alternatively, other securing or locking structure such as a clip or an adaptor, for example, may be employed to join the syringe to the jacket.

In the preferred embodiment of the present invention, the threads are engageable in a limited number of angular positions to thereby predetermine the angular orientation of the syringe in the pressure jacket. Additionally, other keys and keyways carried respectively by the unit and by the syringe limit the angular position in which the syringe may be inserted into the jacket to a unique predetermined angular orientation. Preferably, three keyways, such as slots or notches, unequally spaced around the back, rearward or proximate edge of the syringe body, engage similarly spaced keys or tabs on the unit at the rear end of the pressure jacket to permit insertion of the syringe into the jacket in one and only one orientation.

Further in accordance with principles of the present invention, in its preferred embodiment, a coupling on the syringe plunger is centrally located and symmetrical about the axis of the plunger. A par of jaws on the plunger drive is moveable either by transverse straight or arcuate translatory motion or by forward longitudinal motion to form a connection between the coupling and the drive. Once coupled to the drive, the coupling remains engaged to the drive during longitudinal motion of the drive to cause the plunger to move forward or backward with the drive. Disengagement occurs thereafter only upon transverse translational motion of the plunger with respect to the drive. In certain embodiments, this translatory transverse motion occurs by translatory movement of the jacket, and the injector unit door that carries the jacket, with respect to the plunger drive and the unit housing. In other embodiments, an asymmetrical coupling is provided that engages and disengages the plunger drive upon rotational movement of the syringe with respect to the drive.

Preferably, the motion for locking the syringe to, and unlocking the syringe from, the jacket is achieved by rotation of the syringe in the jacket, and preferably, this motion is linked to, and occurs simultaneous with, the motion that engages and disengages the plunger coupling and drive, whether that coupling is by translation or rotation. In addition, the syringe and plunger drive are so dimensioned and positioned to prevent contact between the drive and the sterile interior wall of the syringe, regardless of the position of the drive, as the syringe is being loaded.

Preferably, the syringe is formed of a cylindrical body, with the front end in the shape of a truncated cone that terminates in a forwardly extending neck with an orifice at its remote end that is connectable with an injection tube. The front end of the syringe is shaped so as to direct fluid leaking from the nozzle outwardly around the front end of the jacket. This prevents leakage, which often results upon disconnection of the injection tubing, from entering the space between the pressure jacket and the syringe body.

Replacement of the syringe begins, in the preferred embodiments of the invention, with the unlocking the syringe at its front end from the front end of the pressure jacket, preferably by rotating the syringe with respect to the jacket, and by disengaging the plunger drive from the syringe plunger, alternatively by transverse translational or rotational motion, preferably simultaneous with and linked to the motion that disengages the syringe from the jacket. The unlocking of the syringe from the jacket occurs, for example, by loosening mating threads at the front of the syringe and jacket. The twisting of the syringe in the jacket is linked to motion that either translates transversely or rotates a coupling on the syringe plunger out of engagement with the plunger drive.

Then the syringe is removed from the jacket through the open front end of the jacket. This removal may take place without retraction of the plunger drive, should the drive be advanced in the pressure jacket at the time of disengagement from the plunger coupling. The used syringe may also be removed without disconnection of the disposable injection tubing from the nozzle of the syringe.

When the used syringe is removed, a replacement syringe is inserted into the jacket through its open forward end and the front end of the new syringe is locked to the front end of the jacket, preferably by relative rotation of the syringe in the jacket to cause, for example, engagement between mating threads on the front end of the syringe and the front end of the jacket. The plunger drive, in one embodiment, is translated to bring the plunger coupling engaging jaws into alignment with the plunger coupling, preferably simultaneously with the locking of the syringe to the jacket. The jaws thereby either engage the coupling upon the translatory motion, or thereafter engage the coupling by longitudinal advancement of the drive against the coupling. In one embodiment, the jaws are positioned off center of the drive so that the drive, whether in the engaging or the disengaging positions, does not contact a syringe as the syringe is guided by the jacket during loading.

In an alternative embodiment, engagement of the plunger drive with the coupling occurs by relative rotation of the drive and the coupling, preferably by rotating the coupling relative to a stationary plunger drive, rather than by translational motion between the drive and the coupling. Only if the rest position of the plunger of the replacement syringe is behind the final position of the plunger drive at the time it was disconnected from the coupling of the plunger of the syringe being replaced need the plunger drive be retracted.

The engagement and disengagement motions between the plunger drive and plunger drive coupling, and between the syringe and the pressure jacket, are provided with manually operable mechanism that, in the preferred and illustrated embodiments, rotates the syringe in the jacket and further either rotates or translates the coupling with respect to the plunger drive, with a simple one hand operated mechanism. The mechanism provides a convenient lever, operable through a short arc, to rotate the syringe in the jacket and to then, preferably, translate the pressure jacket that carries the syringe and is carried by the injector unit door, or to otherwise move the syringe with respect to the drive, to bring the plunger coupling of the syringe into or out of alignment with the plunger drive.

The present invention provides a disposable syringe that may be replaced in an angiographic or CT injector with great efficiency and speed. Further, replacement may occur without retraction of the plunger drive of the injector unit. Simple and rapid one hand operation of the engaging and disengaging structure is provided.

These and other objectives of the present invention will be more readily apparent from the following detailed description of the drawings in which:

BRIEF DESCRIPTION OF THE DRAWINGS

FIG. 15 is a cross-sectional view similar to FIG. 5 of an alternative embodiment of the invention, illustrating alternative engaging structure between the front ends of the syringe and jacket.

FIG. 16 is a cross-sectional view similar to FIG. 5 of a further alternative embodiment of the invention, also illustrating alternative engaging structure between the front ends of the syringe and jacket.

FIG. 17 is a front end view of still a further alternative embodiment of the invention, also illustrating alternative engaging structure between the front ends of the syringe and jacket

DETAILED DESCRIPTION OF THE DRAWINGS

Figure 1:
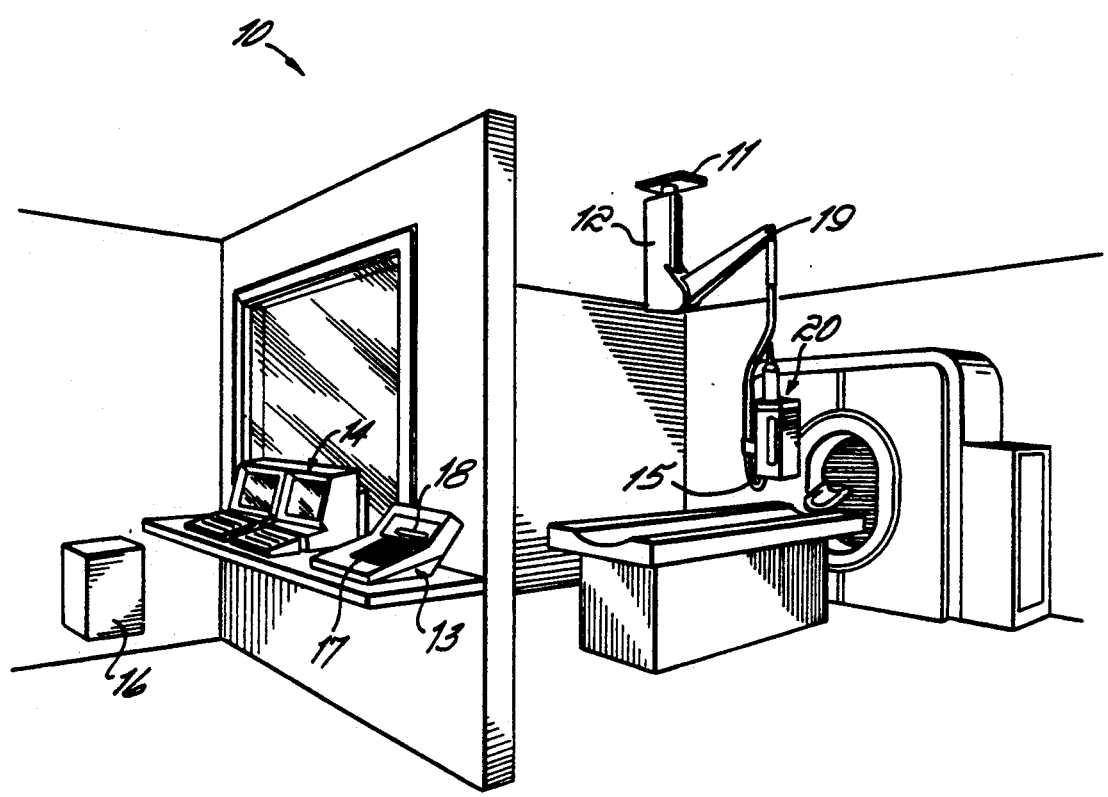
FIG. 1 is a perspective view of an angiographic CT injector embodying principles of the present invention.

Referring to FIG. 1, an angiographic injector 10 according to another preferred embodiment of the present invention is illustrated, configured for CT applications. The injector 10 includes a ceiling mounted support 11, adjacent a CT X-ray unit, to the lower surface of which is rigidly supported a vertically descending support column 12.

Remote from the support 11 is an injector control module console 13 behind a wall which isolates the operator area from the X-ray equipment. The console 13 is located adjacent a control 14 of the X-ray equipment. Electrical power and control cables (not shown) communicate power and control signals through the support 11 and the column 12 and to a power lead 15. The console 13 connects with an injector control module 16, which includes a programmable microprocessor (not shown) to which commands and programming codes are input through a keyboard 17 on the console 13. The console 13 is also provided with an operator display 18 to aid in interfacing the input commands and injector status with the operator.

Attached to the column 12 is an articulating adjustable arm 19. To the remote end of the arm 19 is adjustably supported injection module unit 20. The arm 19 is capable of setting the unit 20 at varying positions adjacent a patient bed of the CT unit.

Figure 1A:
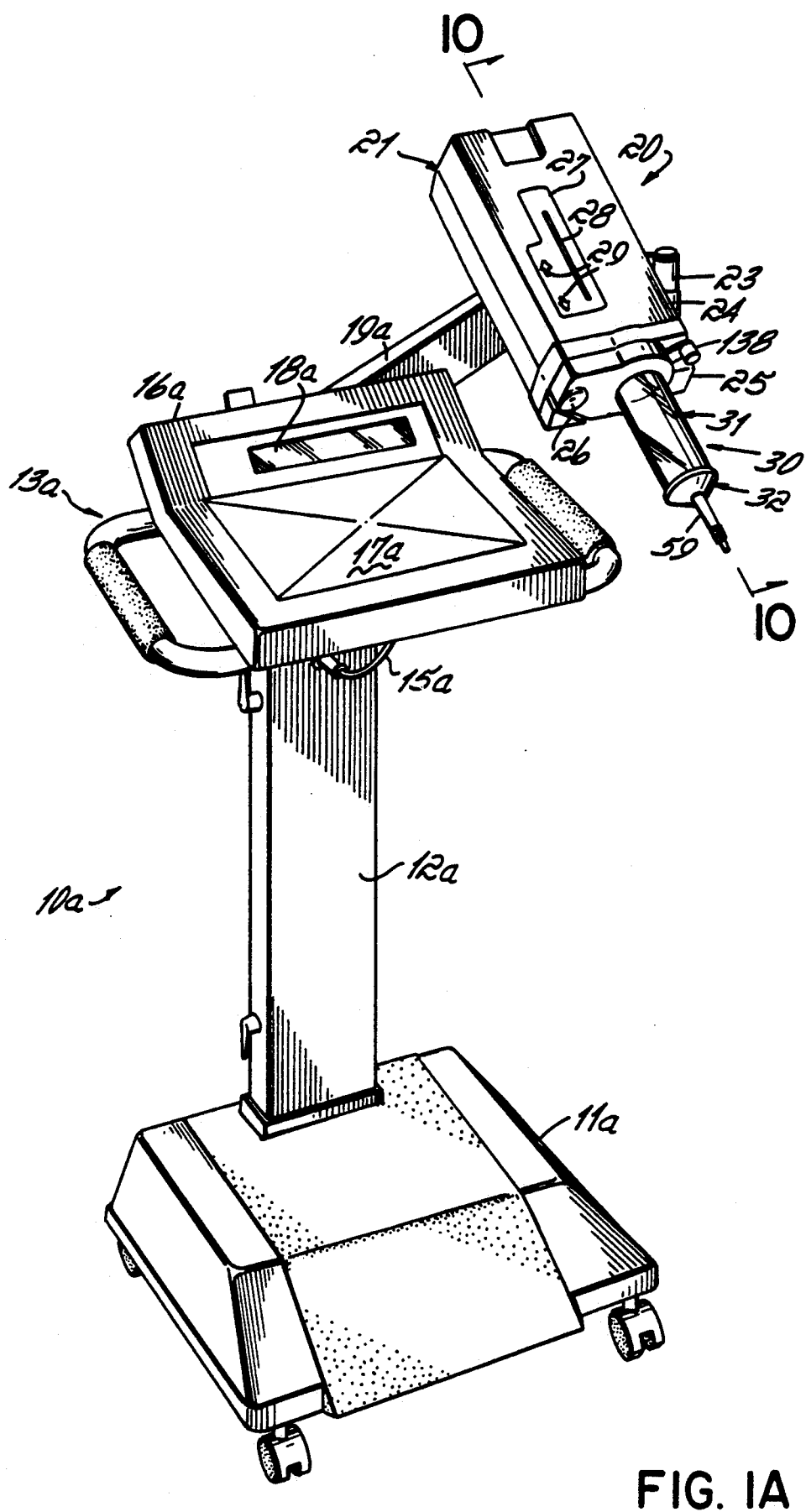
FIG. 1A is a perspective view of an another form of angiographic injector embodying principles of the present invention.

Referring to FIG. 1A, an angiographic injector 10a according to another preferred embodiment of the present invention is illustrated. The injector 10a includes a wheeled base 11a to the top of which is rigidly supported a vertically adjustable upstanding support column 12a. To the top of the column 12a is supported a control module platform 13a. Electrical power is communicated from a power cord (not shown) through the base 11 and the upstanding support 12a and through a power lead 15a to a control module 16a rigidly supported to the platform 13a. The control module 16a includes a programmable microprocessor (not shown) to which commands and programming codes are input through a keyboard 17a on the module 16a. The module 16a is also provided with an operator display 18a to aid in interfacing the input commands and injector status with the operator. Attached to the platform 13a is an articulating adjustable arm 19a. To the remote end of the arm 19a is adjustably supported the injection module unit 20.

The injection module unit 20 of the embodiments of FIGS. 1 and 1A includes a housing 21 which contains the operating drive structure of the injector 10 or 10a.

The housing 21 has a support bracket 23 fixed thereto and adjustably pivotally supported to the remote end 24 of the articulating arm 19 or 19a. The housing 21 has pivotally attached to the front thereof a door 25 at the front thereof which is pivotally connected to the housing 21 at a longitudinally extending pivot or hinge pin 26 (FIG. 2) rigidly supported on the housing 21 and extending forwardly from the front of the housing 21.

On the top of the housing 21 is an injector position and local control panel 27 having a position indicator scale 28 thereon, which displays the position of the injector drive to the operator. The panel 27 also includes a pair of forward and reverse drive direction control buttons 29, which are selectively actuatable to activate a drive within the housing 21 in either the forward or reverse directions.

Extending forwardly from the front of the door 25 is an injector syringe and pressure jacket assembly 30, the structure of which can be better understood with reference to FIGS. 2–5 below. The syringe and jacket assembly 30 includes a hard plastic pressure jacket 31, which may be of opaque or transparent material, a removable and replaceable disposable syringe 32, which may be of opaque, transparent or semi-transparent material, and related structure hereinafter described.

The syringe 32 is disposable, and includes walls which will withstand only moderate or low pressure. The walls are usually outwardly deformable under operating pressures, particularly pressures of 300 psi or more. Such higher pressures are necessary to overcome pressure drops through the injection tubing at higher flow rates, which are often desirable. The jacket 31 is made of a stronger transparent material that will withstand the operating pressures. When the syringe 32 is contained in the jacket 31, it is surrounded by the jacket 31 and supported by the jacket 31 against expansion caused by the fluid pressure within as the syringe 32 expands against the jacket wall.

Figure 2:
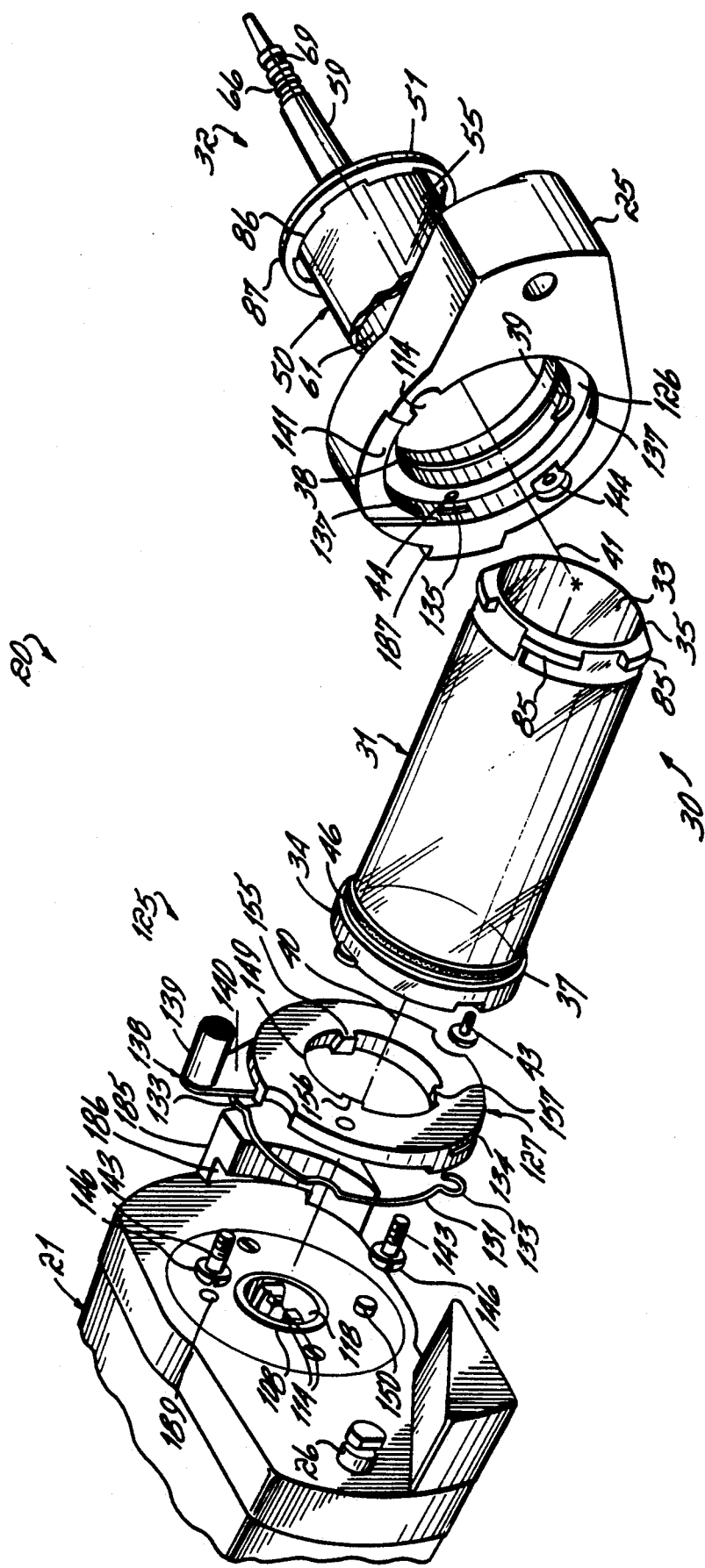
FIG. 2 is an exploded perspective view of a portion of one preferred embodiment of the injector of FIG. 1.

The pressure jacket 31 has a generally cylindrical inner bore 33 extending therethrough from a proximate end 34 adjacent the door 25 to a remote end 35 of the pressure jacket 31 toward the front of the unit 20. The bore 33 is dimensioned so as to receive through the remote end 35 the disposable syringe 32 and to support the syringe against expansion from fluid pressure within such fluid pressure may range to more than a thousand psi. The pressure jacket 31 has an annular flange 37 extending outwardly around the proximate end 34. The flange 37 is integrally formed with the jacket cylinder and is shaped to conform to an annular recess 38 surrounding a circular hole 39 in the door 25 to which the jacket 31 may be assembled by insertion from the rear. The hole or opening 39 in the door 25 and the cylindrical bore 33 of the jacket 31 are concentric with a longitudinal axis 40 on which also lies an axis 41 of the syringe 32 when the syringe 32 is positioned in the bore 33 of the jacket 31. The jacket 31 is firmly and rigidly attached to the door 25 with a pair of screws 43, only one of which is shown, which are threaded into a pair of holes 44 in the back of the door 25 (FIG. 2). An O-ring seal 46 surrounds the flange 37 of the jacket 31 in the recess 38 of the door 25.

Figure 3:
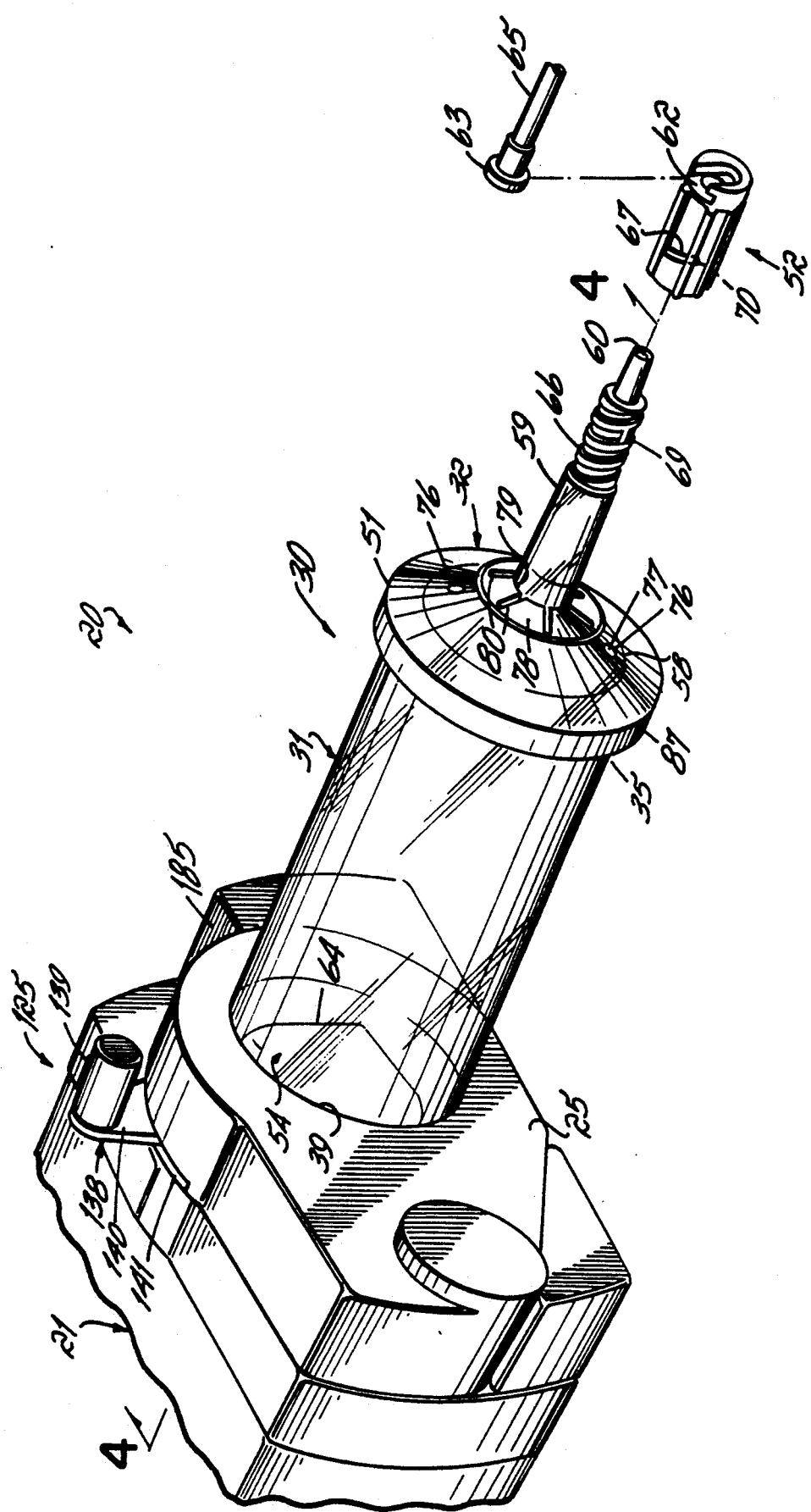
FIG. 3 is a perspective view of the portion of the injector of FIG. 2.
Figure 4:
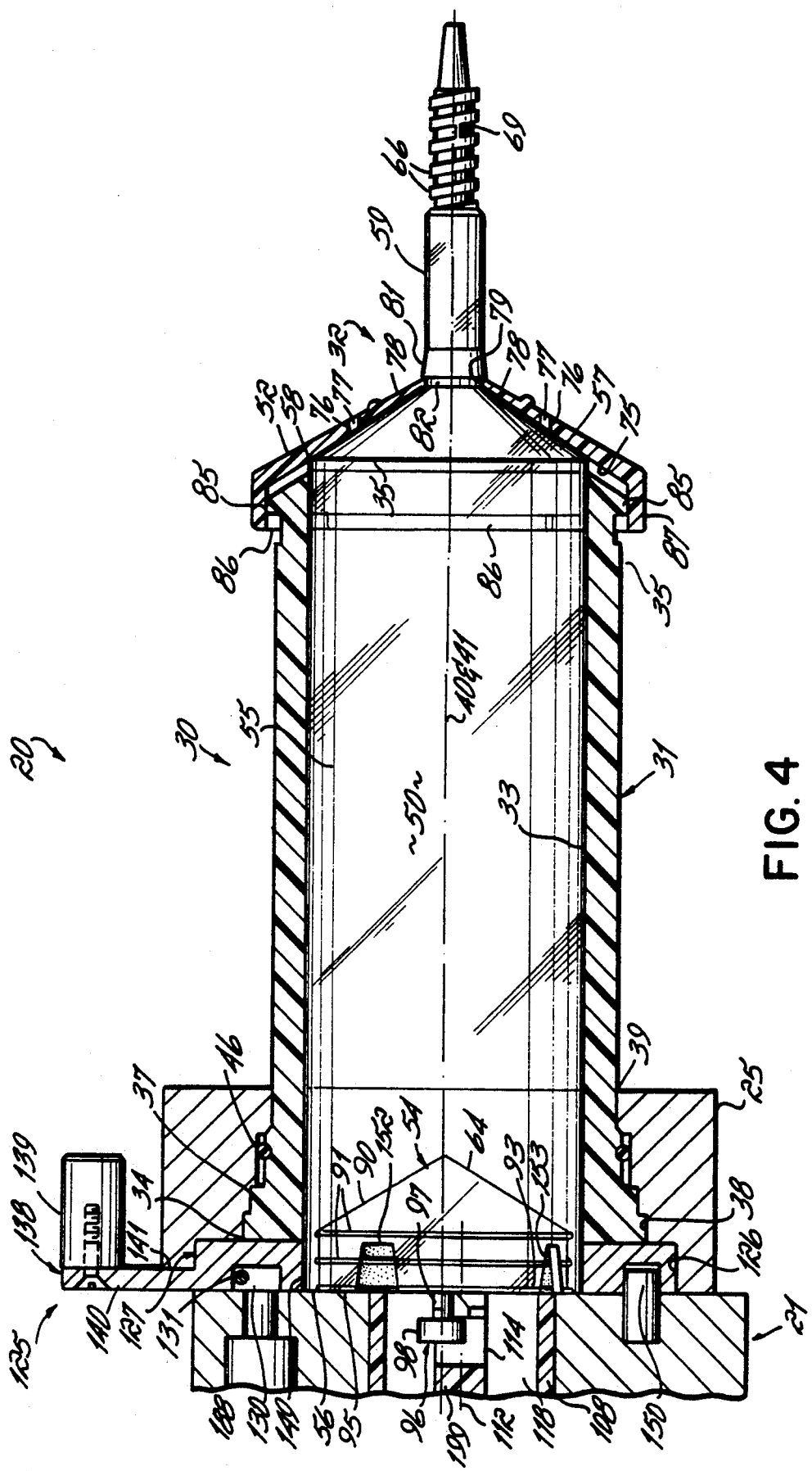
FIG. 4 is a cross-sectional view along lines 4—4 of FIG. 3 illustrating a replaceable syringe unlocked from the housing for insertion into or removal therefrom.
Figure 5:
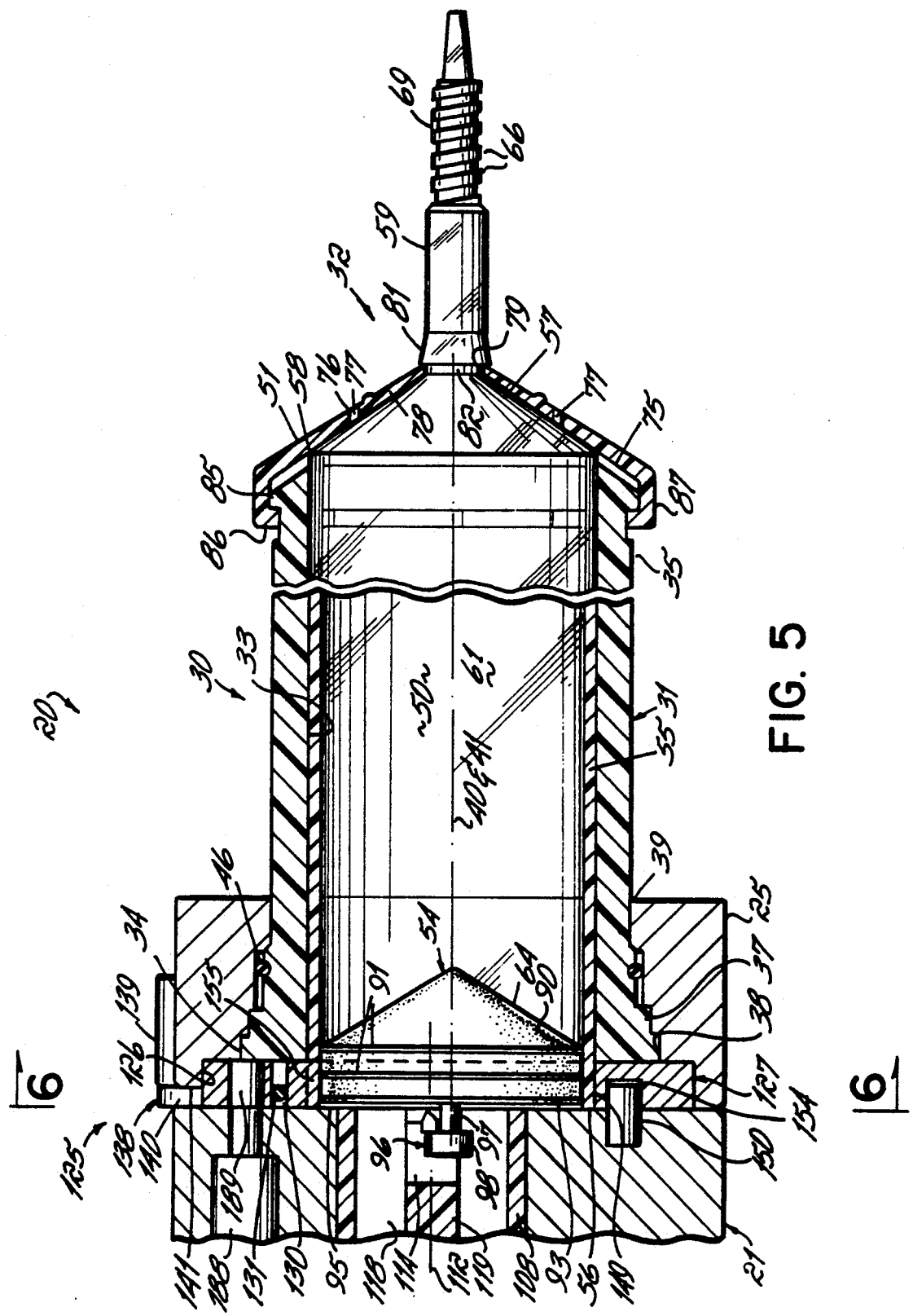
FIG. 5 is a cross-sectional view similar to FIG. 4 but illustrating the syringe locked to the structure carried by the housing.

The syringe 32 includes a syringe case 50 formed of a single piece of molded plastic material, a pressure cap 51, a tubing collar 52 (FIG. 3) and a plunger 54 (FIGS. 3–5). The syringe case 50 includes a cylindrical syringe body 55 having an open proximate end 56 and a remote end 58 to which is integrally formed a conical front wall 57. The front wall 57 is truncated at its forward end, to which is integrally formed an elongated neck 59 extending from the wall 57 at the center thereof. The neck 59 of the syringe case 50 has an orifice 60 (FIG. 3) in its remote end which communicates with an internal syringe cavity 61 formed within the neck 59, the conical front wall 57 and the cylindrical body 55 of the case 50 of the syringe 32. The rear end of the cavity 61 is further defined by a forward facing conical surface 64 of the plunger 54. The conical surface 64 is of a slope which conforms to the slope of the interior of the conical front wall 57. The plunger 54 is slidable within the body 55 of the syringe case 50 such that the cavity 61 is of variable volume.

Near the front end of the neck 59 of the syringe case 50, just behind the orifice 60, is an external thread 66 configured to mate with threads 67 on the interior of collar 52 (FIG. 3). The thread 66 in the neck 59 has an stop 69 at near forward end thereof to engage an abrupt step 70 on the thread 67 of the collar 52 so that, when the syringe 32 is properly oriented in the jacket 31, the collar 52, when loosened to its maximum extent, will assume a predetermined orientation so as to present, in an upwardly facing orientation, a tube end receiving slot 62 formed in the remote end of the collar 52. This slot 62 is of T-shaped cross-section so as to receive the enlarged flange end 63 of a tube 65 through which fluid from the syringe cavity 61 is injected into a patient The cap 51 is generally conical in shape and has an inner rearward surface 75, which conforms to the front surface of the conical wall 57 of the case 50 of the syringe 32. In certain embodiments, the rearward conical surface 75 of the cap 51 may be bonded to the front surface of the conical wall 57 of the case 50 of the syringe 32, or it may be formed integrally therewith, molded from the same plastic material as the case 50 of the syringe 32. In the preferred and illustrated embodiment, the cap 51 is separate from the syringe body portion 55 and has a pair of holes or detents 76 into which fit a pair of projections 77 extending forwardly from and formed integrally on the outer surface of the conical wall 57 of the case 50 of the syringe 32. The cooperation of the pins or projections 77 with the holes or detents 76 prevent the cap from rotating with respect to the syringe case 50 when the cap 51 is mounted on the syringe 32.

To hold the cap 51 against the conical wall 57 of the case 50 of the syringe 32, six resilient tabs 78 are formed about a central inner hole 79 of the cap 51. The tabs 78 are separated by six equally spaced radial slots 80 (FIG. 3). The hole 79 in the cap 51 is equal to or only slightly greater in size than the circular forward end of the conical wall 57 of the case 50 of the syringe 32. The neck 59 of the syringe 32 has an enlarged straight section 81 slightly greater in diameter than the hole 79 in the cap 51 and also greater in diameter than the forward end of the conical wall 57 of the case 50, thereby forming a groove 82 at the juncture of the straight neck portion 81 with the conical wall 57 so that the tips of the tabs 78, which are sufficiently resilient to slide over the enlarged neck portion 81 as the cap 51 is inserted on the case 50 of the syringe 32 with the hole 79 surrounding the neck 59 to snap fit into the groove 82.

The syringe 32 includes structure that is configured to lock the syringe 32 to the front end of the jacket 31 by cooperating with mating structure on the jacket 31. The jacket 31 has, spaced around the circumference thereof near the remote or front end 35 of the jacket 31, four equally spaced outwardly projecting thread sections 85. These thread sections 85 are slightly less than 45° in extension around the circumference of the jacket 31 and are spaced apart with gaps of slightly greater than 45°. The cap 51 has a cylindrical rim 87 in which are formed four similarly sized and spaced mating thread sections 86. The thread sections 86 project inwardly toward the jacket 31 when the syringe 32 is positioned in the jacket 31. As such, when the syringe 32, with the cap 51 assembled to it is inserted into the jacket 31, the threads 86 of the cap 51 pass through the spaces between the threads 85 on the jacket 31 to a point behind the threads 85. When so inserted, the syringe assembly 32 with the cap 51 may be twisted clockwise 45° to tighten and thereby secure the cap 51 to the jacket 31 by engagement between the threads 85 and 86 as shown in FIG. 5, to thereby lock the syringe in the bore 33.

The piston 54 of the syringe 32 is molded of an elastomeric material. Preferably, the piston 54 includes two portions molded of different materials and bonded together. These portions include a forward more flexible portion 90 in which is formed the forward conical surface 34. This forward portion 90 has a pair of outwardly extending rings 91 formed in the periphery thereof to make sealing engagement with the inside of the wall of the cylindrical body 55 of the syringe case 50. The rearward portion of the piston 54 is a flat circular surface to which is bonded the flat circular forward surface of a more rigid rear portion 93 of the piston 54. The rear rigid portion 93 of the piston 54 is molded of a harder stronger plastic material and has a rearward facing circular surface 95 having a rearward extending coupling 96 integrally formed thereon at its center. The coupling 96 includes a rearwardly extending cylindrical shaft 97 on the axis 41 of the syringe 32 and a larger symmetrical cylindrical button 98 integrally formed at the rear end of the cylindrical shaft 97.

Figure 10:
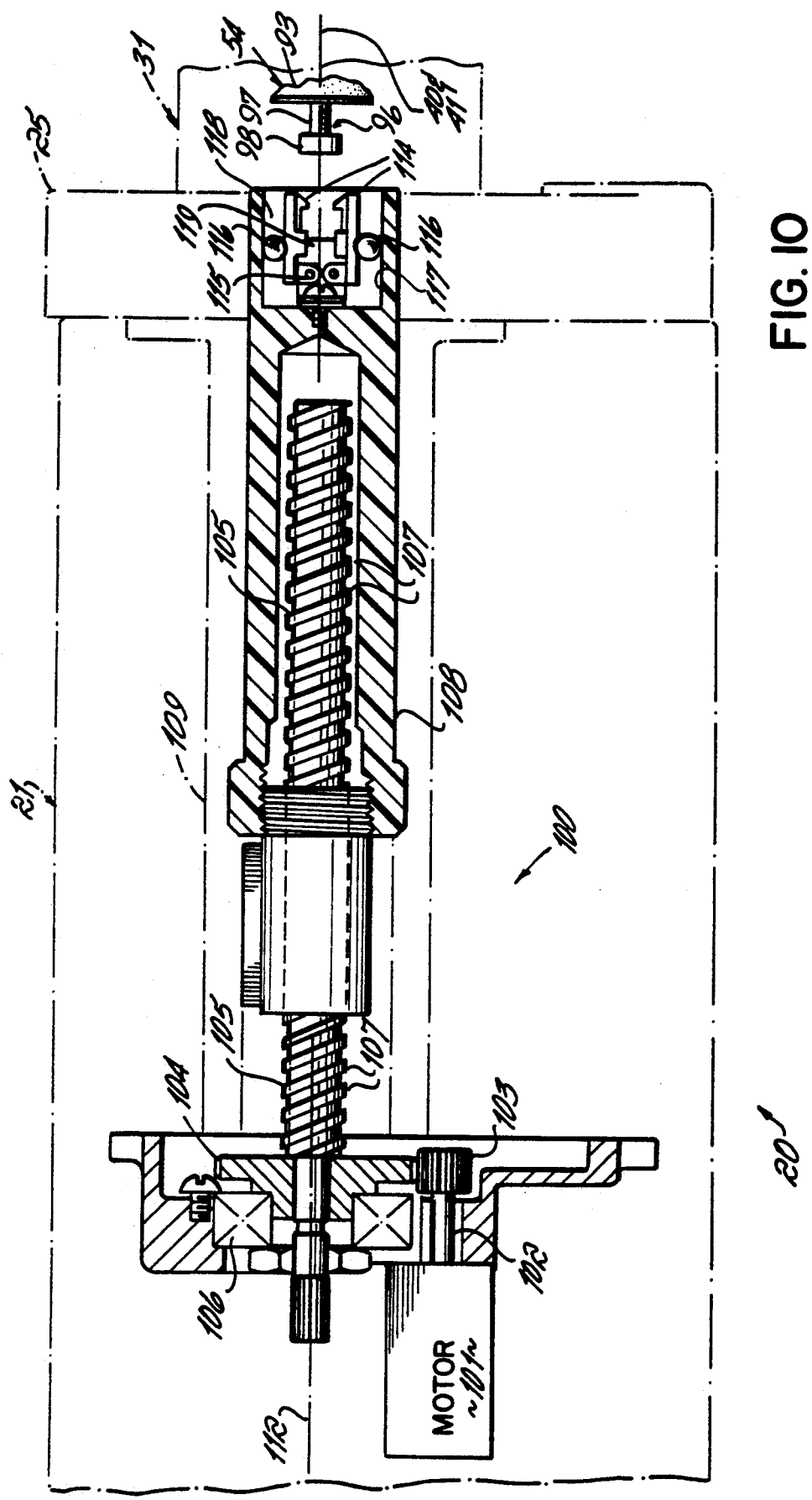
FIG. 10 is a cross-sectional view through the housing of the injector taken along lines 10—10 of FIG. 1 with the plunger drive disengaged from the syringe plunger coupling.

Referring to FIG. 10, a piston drive assembly 100 is illustrated contained within the housing 21. The drive assembly 100 includes an electric motor 101 mounted within the fixed housing 21 and having a rotary output shaft 102 with a drive gear 103 fixed to the remote end thereof. The drive gear 103 is positioned for driving engagement with a driven gear 104 fixed near the rear end of a drive screw or shaft 105 supported at its rear end in a bearing 106 fixed in the housing 21. The screw or shaft 105 has a continuous external helical thread 107 thereon which mates with interior threads of a carriage 108. The carriage 108 is slidably supported in a bushing 109 fixed in the housing 21. The shaft 105 rotates within the housing 21 about a longitudinal axis 112.

At the forward end of the carriage 108 is supported a pair of hooked jaws 114 which are pivotally mounted at their rearward ends by a pair of pivot pins 115 to the carriage 108. The jaws 114 are biased toward the axis 112 by a pair of balls 116a and 116b of resilient material positioned between the outside of the jaws 114 and an inner cylindrical wall 117 of a recess 118 formed in the forward end of the carriage 108. The balls 116a, 116b are partially captured in depressions in the outer surfaces of the jaws 114. The balls 116a, 116b bias the jaws toward their innermost position toward the axis 112. The innermost position of the jaws is determined by a spacing block 119 on the axis 112 of the carriage 108 at the center of the cavity 118.

When a syringe 32 is locked in the jacket 31 with its axis 41 and the axis 40 of the jacket 31 may be in alignment with the axis 112 of the shaft 105, the plunger 54 may be located in the cylindrical body 55 of the syringe case 50 in a position forward of the remote end 56. Preferably, however, the jaws 114 are displaced to the side of axis 112 of the shaft 105 so that as the jaws 114 and coupling tip 98 are in their disengagement position, maximum clearance is provided so that the syringe 32 may be inserted into the jacket 31 without the sterile internal walls of the syringe 31 touching the components of the drive, as illustrated in the figures.

Figures 6, 11, 12:
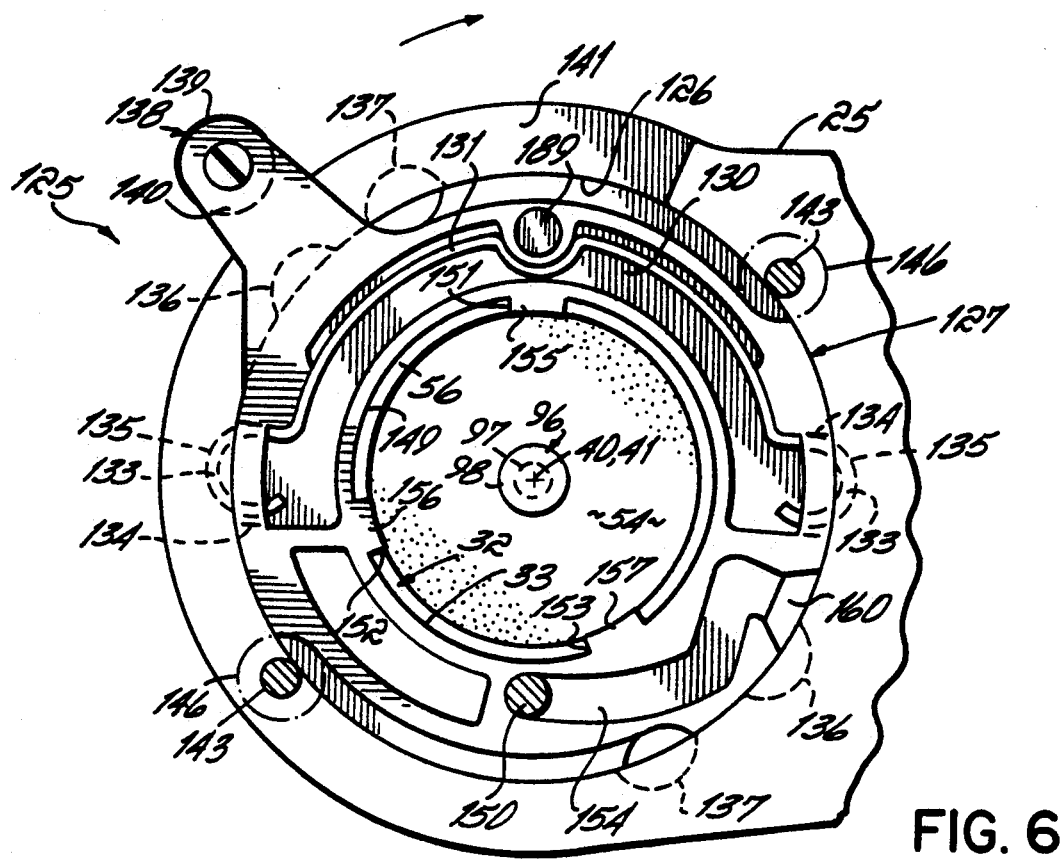
FIG. 6 is a cross-sectional view along the line 6—6 of FIG. 5.
FIG. 11 is a view of a portion of FIG. 10 illustrating the plunger drive longitudinally moving into engagement with the plunger coupling.
FIG. 12 is a view of a portion of FIG. 10 illustrating the plunger drive in engagement with the plunger coupling.

In the engaging position, the jaws 114 are nonetheless in alignment with the coupling 98 on the axes 40 and 41 of the jacket 32 and syringe 32. In such a situation, the jaws 114 may be in a retracted position at the center of the opening 39 of the door 25 adjacent to the proximate end 34 of the jacket 31, and out of engagement with the coupling 96 on the plunger 54. From this position, operation of the motor 101 rotates the shaft 105 and drives the carriage 108 forwardly to move the jaws 114 toward and into engagement with the coupling 96 on the plunger 54. This engagement takes place as shown in FIG. 11 where a pair of tapered cam surfaces 120 at the forward interface of the tips of the jaws 114 engage the enlarged portion or button 98 of the coupling 96 to expand the jaws, as shown in FIG. 11, to snap around the button 98 of the coupling 96 to form a driving engagement between the drive assembly 100 and the coupling 96 of the plunger 54 as shown in FIG. 12. Once so engaged, any forward or reverse movement of the carriage 108 under the power of the motor 101 will cause the plunger 54 to be driven either forwardly or backwardly in the syringe body 55.

Disengagement of the jaws 114 from the coupling 96 can thereafter be achieved by translational movement between the coupling 96 and the jaws 114 between a disengaged position as shown in FIG. 4 and an engaged position as shown in FIG. 5. When the plunger coupling 96 and the jaws 114 are disengaged, the syringe 32 can be replaced without the need to retract the carriage 108 of the drive 100. This allows for rapid replacement of the syringe 32. Preferably, the jaws 114 are either fully retracted toward the housing 21 where engagement by translation of the coupling 96 will occur, or the jaws 114 are sufficiently within the jacket prior to replacement of the syringe so that the coupling 96 of the replacement syringe 32 will not contact the jaws 114 except as the drive 100 is advanced.

If sterility is not a problem, the most time saving approach would be to insert the syringe 32 into the jacket 31 with its plunger all the way forward and the drive fully advanced so that, when the syringe is translated toward the jaws 114, engagement will immediately occur and the plunger can be immediately retracted to fill the syringe.

When a syringe 32 is inserted into the jacket 31 when the plunger 54 is at its rearmost position toward the proximate end 56 of the syringe body 55, the coupling 96 is in a position adjacent the proximate end 56 of the syringe body 55 and projecting rearwardly therebeyond. When in such a position, engagement between the jaws 114 and the coupling 96 is brought about by translational movement between the position shown in FIG. 4 and that shown in FIG. 5. In the unlocked or disengaged position shown in FIG. 4, the axes 40 and 41 of the jacket 31 and the syringe 32, respectively, as well as the center of the opening 39 of the door 25, lie spaced from and parallel to the axis 112 of the shaft 105 as shown in FIG. 4. In the locked or engaged position, the axis 112 of the shaft 105 is slightly eccentric relative to the axes 40 and 41 of the jacket 31 and syringe 32, respectively, as shown in FIG. 5. This translational movement, the engagement and disengagement between the coupling 96 and the jaws 114 and the 45° rotational movement which secures the cap 51 to the pressure jacket 31 by engagement of the threads 85 and 86 are brought about by operation of a translating and locking mechanism 125, which is best understood by reference to FIGS. 2-9.

The translating and locking mechanism 125 includes a cam and locking ring 127 which is rotatably retained in a circular recess 126 in the back of the door 25. The ring 127 has a generally semi-circular groove 130 in the back surface thereof for receiving a spring wire retaining clip 131 having a pair of looped ends 133 which extend through a pair of slots 134 in the rim of the ring 127 and into a selected one of three pair of diametrically opposed notches 135, 136 and 137 in the inner wall of the rim of the recess 126 in the door 25. The three pair of notches 135, 136 and 137 represent three positions of the translating and locking mechanism 125 which are the locked, unlocked and release positions, respectively. The locked position of the mechanism 125 in which the loops 133 of the ring 131 are in the notches 135, is that illustrated in FIGS. 5-7 and 10. The unlocked position, in which the loops 133 of the ring 131 are in the notches 136, is that illustrated in FIGS. 2-4 and 8. The release position, in which the loops 135 of the clip 133 are in notches 137, is that illustrated in FIG. 9. The ring 127 is moved among these three positions by a manually accessible handle 138 in the form of a cylindrical knob 139 rotatably attached to a lever arm 140 formed integrally and extending radially from the ring 127 through a slot 141 in the door 25 (FIG. 1). The ring 127 is retained in the recess 126 by a pair of screws 143 which thread into countersunk holes 144 at the periphery of the recess 126 in the back of the door 25. These screws 143 have enlarged heads 146, which, when seated in the holes 144, overlie the edge of the ring 127, thereby securing it for rotatable movement within the recess 126.

As shown in FIGS. 2 and 6, the ring 127 has an inner periphery 149 which is larger than the circumference of the body 55 of the syringe case 50. Accordingly, when the syringe 32 is inserted in the jacket 31, the proximate end 56 of the syringe case 50 extends through and is surrounded by the inner periphery 149 of the ring 127. Asymmetric keyway structure, preferably in the form of three slots or notches 151, 152 and 153 (FIG. 6) are provided in the edge of the proximate end 56 of the body 55 of the syringe case 50. The spacings between adjacent pairs of the notches 151-153 differ from each other. Formed integrally of the ring 127 and projecting inwardly from the inner periphery 149 thereof are three tabs or keys 155, 156 and 157. These tabs 155-157 are spaced so as to fit into the respective notches 151-153 in the proximate end 56 of the body 55 of the syringe case 50 so as to rotate the syringe 32 as the mechanism 125 is rotated through actuation of the handle 138. Because the notches 151-153 and the tabs 155-157 are unequally spaced, they can only engage each other when the syringe 32 is inserted into the jacket 31 in one and only one orientation. That orientation is one which will cause the slot 62 of the collar 52 (FIG. 3) to align 45° counterclockwise of the vertical when the mechanism 125 is in its unlocked position, which is a position in which it will be when the syringe is first inserted into the jacket 31, and to be in an upwardly facing orientation, when fully loosened, when the mechanism 125 is moved to its locked position. Accordingly, the notches 135 and 136 in the recess 126, which receive the loops 133 of the spring clip 131 when respectively in the locked and unlocked positions, are 45° apart.

The rotation of the mechanism 125 from the unlocked position to the locked position rotates the syringe 32 in the jacket 31 and rotates the cap such that its threads move from an unlocked position as shown in FIG. 4 to the locked position of FIG. 5, to secure the cap to the jacket 31 by the engagement and tightening of the threads 85 and 86.

The translational movement of the axes 40 and 41 with respect to the axis 112 is achieved by a fixed cylindrical cam follower or pin 150 which projects outwardly from the fixed housing portion 22 behind the ring 127 and into a cam slot 154 formed therein. The slot 154 is shaped so that the axes 40 and 41 which remain fixed with respect to the ring 127, along with the door 25, the jacket 31, the syringe 32 and all of the structure mutually carried thereby, are moved in relation to the axis 112 of the shaft 105 and the other structure mutually carried by the housing 22, as the mechanism 125 is rotated. These axes move toward and away from each other in accordance with the shape of the slot 154 determined by the radial distance from the point along the slot 154 where it engages the pin 150 to the axes 40 and 41.

Figure 7:
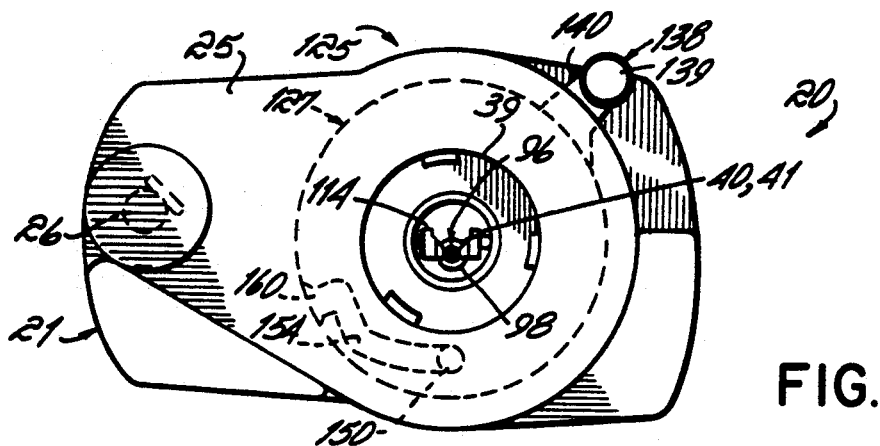
FIG. 7 is an elevational diagrammatic illustration of the injector of FIG. 1 with the pressure jacket and syringe removed, and showing the syringe locking structure in the locked position such as in FIGS. 5 and 6.
Figure 8:
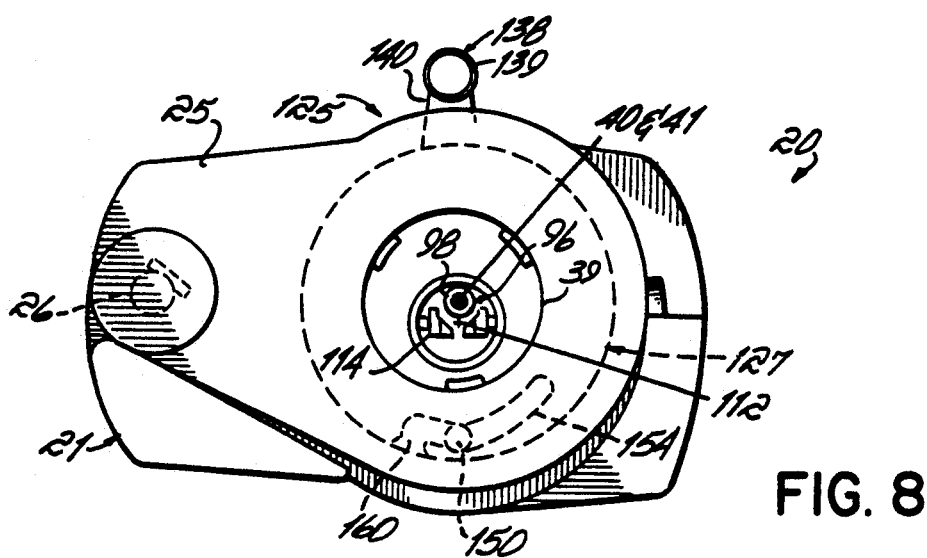
FIG. 8 is an elevational diagrammatic view similar to FIG. 7 illustrating the syringe locking structure in the unlocked position such as in FIGS. 2-4.

The cam slot 154 in the ring 127 is shaped such that, when the mechanism 125 is in the locked position as shown, for example, in FIGS. 6 and 7, the distance between the pin 150 and the axes 40 and 41 is at a minimum and the axis 112 coincides with the axes 40 and 41. This is illustrated in FIGS. 5 and 7 wherein the coupling 96 is shown positioned between the jaws 114 and in mutual engagement therewith. When the mechanism 125 is in the unlocked position, with the loops 133 of clip 131 in the notches 135 (FIG. 6) of the recess 126, the pin 150 lies in the slot 154 in the position shown in FIG. 8, which is farther displaced from the axes 40 and 41 than in the position of FIGS. 6 and 7, so that the coupling 96 is translated to a position outside of the center line of the jaws 114, as shown in FIG. 8 and further illustrated in FIG. 4.

Figure 9:
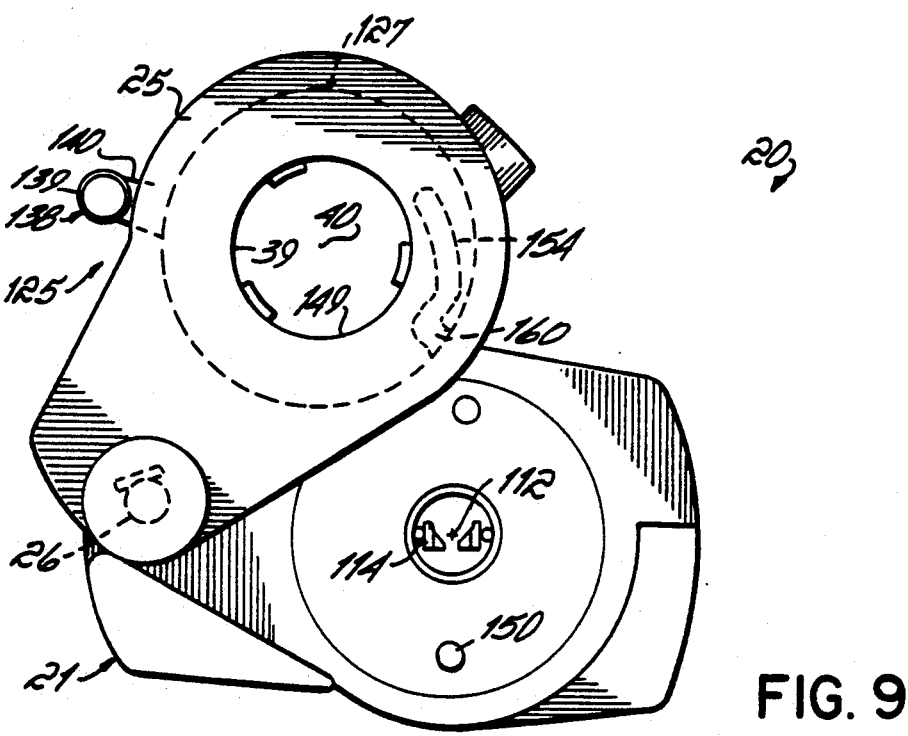
FIG. 9 is an elevational diagrammatic view similar to FIG. 7 illustrating the locking mechanism in the housing door release position.

In the release position, as shown in FIG. 9, the pin 150 is positioned at the open end 160 of the cam surface of the slot 154 so that the door 25 can be rotated upwardly about the hinge pin 26, as shown in FIG. 9, to open the space behind the door 25 for access thereto. This position may be used for cleaning the area behind the door 25 which is sometimes necessary because of possible leakage of fluid from the cavity 61 into the space behind the plunger 54. This can possibly occur because the fluid within the cavity 61, when being injected by forward advancement of the plunger 54, may be of relatively high pressure in the range, usually over 200 psi. For applications such as the injection of contrasting fluid for CT scanning, pressure may typically be in the range of from 25 to 300 psi., while in some angiographic injection applications the pressure may range to 1200 psi or higher.

In addition, leakage rearwardly along the exterior of the neck 59 of the syringe 32 can cause fluid to flow between the body portion 55 of the syringe 32 and the jacket 31. For this reason, the cap 51 is caused to fit snugly against the forward surface of the conical portion 57 of the syringe 32 at least sufficiently to restrict the flow of this leaking fluid onto the neck 59. This is assisted by the configuration of the cap 51 at the rim 87 thereof so as to divert away from the space between the syringe 32 and jacket 31 fluid which might leak from the nozzle.

The front of the housing 21 has formed thereon a door stop 185 having a slot 186 formed therein for receiving a lug 187 of the door 25, to restrain the door 25 against forward force exerted by the drive 100. Behind the front of the housing 21 adjacent the stop 185 is a magnetic sensor 188, which is responsive to the presence of a magnet 189 in the lever arm 139 of the handle 138. The sensor 188 generates a signal to the control module 16 to activate the drive 100 only when the mechanism 125 is in its locked position.

Figure 13:
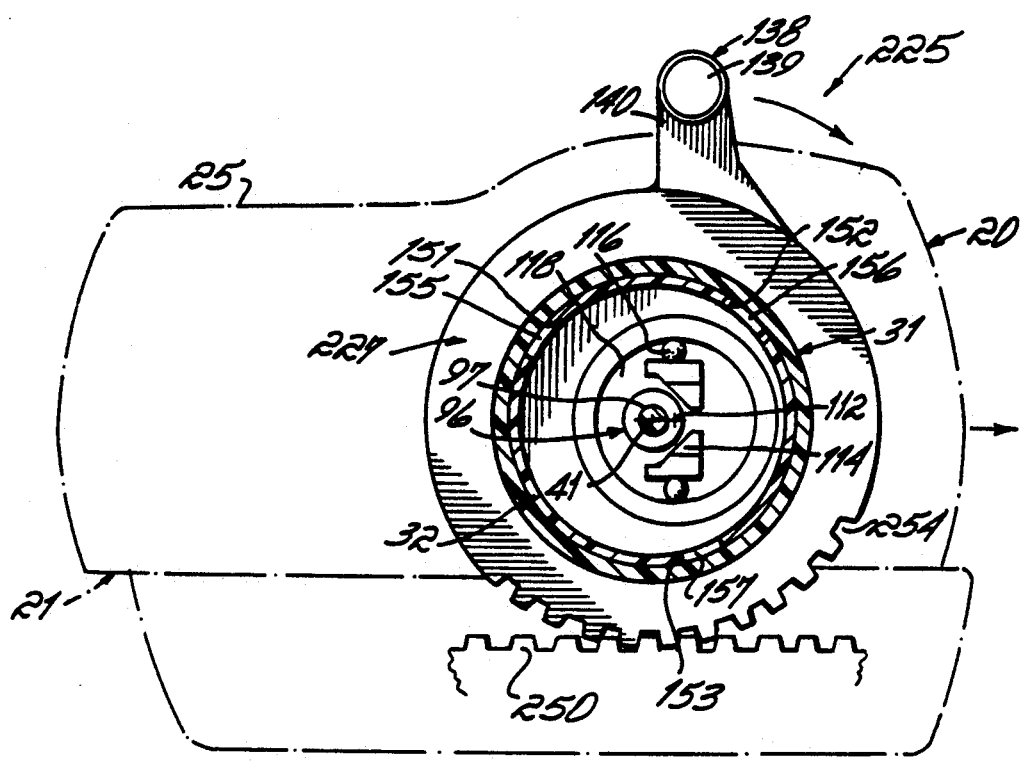
FIG. 13 is a front view of a portion of another embodiment of the injector of FIG. 1.

Referring to FIG. 13, there is illustrated a locking mechanism 225 that is an alternative to the locking mechanism 125 described above. In the locking mechanism 225, a stationary geared rack 250 is provided fixed to the housing 21. A mating gear segment 254 is formed on the outer rim of the alternative locking ring 227 of this embodiment. The gear segment 254 and rack 250 replace and function in the same way as the slot 154 and pin 150 of the embodiment described above. As the mechanism 225 is rotated by the handle 138, the door 25 that carries the jacket 31 and the syringe 32 is translated to bring the coupling 96 into or out of engagement with the jaws 114 of the drive 100. Simultaneous with this translatory motion, the syringe 32 is rotated in the jacket 31 to lock or unlock the syringe 32 to the jacket 31 by engagement or disengagement of the threads 86 on the syringe 32 with the threads 85 on the jacket 32.

Figure 14:
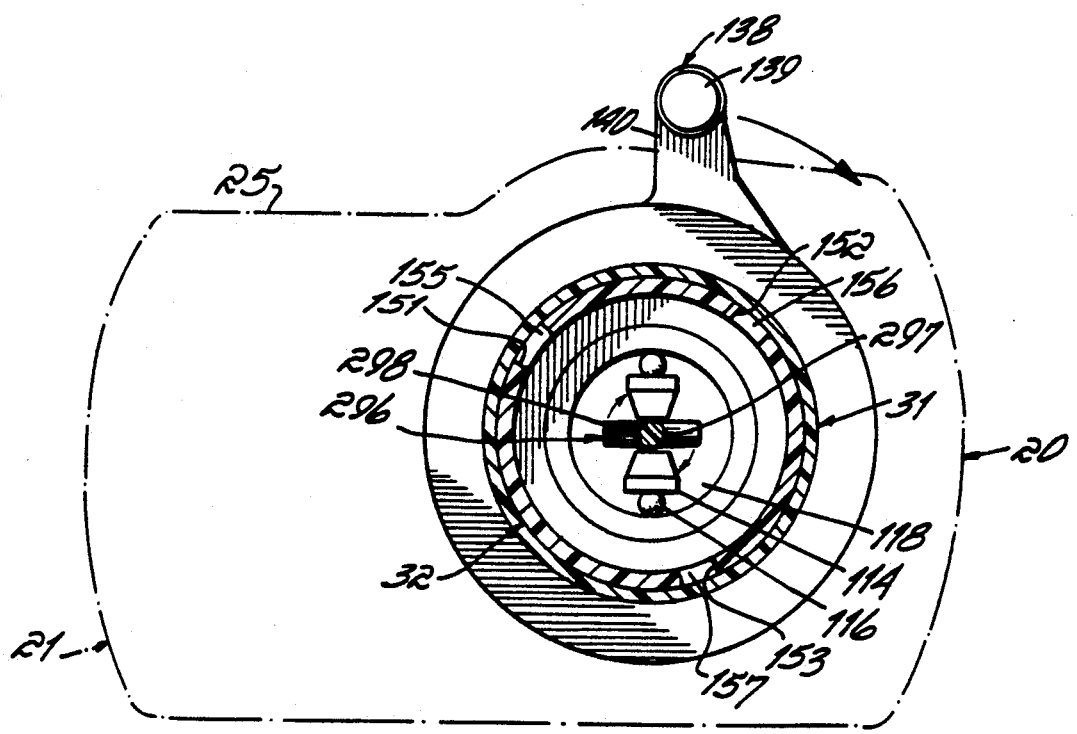
FIG. 14 is a view of an alternative embodiment of a portion of a syringe according to principles of the present invention.

FIG. 14 illustrates an alternative to the embodiment of the coupling 96 described above. In the embodiment of FIG. 14, there is provided a coupling 296 that is T-shaped, having a rectangular endpiece 298 at the rearward end of a cylindrical or square shaft 297 on the rearwardly facing circular surface 95 of the plunger 54. Such a coupling 296 engages the jaws 114 by rotation of the locking mechanism 125 or 225, preferably through an angle of 90°. When the orientation of the endpiece 298 is parallel to the plane of the jaws 114, the drive 100 is locked to the plunger 54 so that axial movement of the drive 100 moves the plunger axially, in the forward direction to expel fluid form the syringe cavity 61, or in a rearward direction to fill the cavity 61 with fluid. When the endpiece 298 is perpendicular to the plane of the jaws 114, the coupling 296 will move into or out of engagement with the jaws 114 upon relative axial movement between the plunger 54 and the drive 100. Thus, with this embodiment, rotational motion, rather than translational motion, causes engagement and disengagement of the coupling 296 by the jaws 114. With this embodiment, orientation of the syringe 32, when loaded into the jacket 31, is preferably maintained through the cooperation of the notches 151-153 and the tabs 154-156 (FIG. 4), so that the coupling 296 will enter the jaws 114, when the syringe 32 is inserted into the jacket 31, with the endpiece 298 perpendicular to the pair of jaws 114.

The locking structure between the syringe 32 and the pressure jacket 31 should provide for retention of the syringe 32 in the jacket 31 against the force of the fluid pressure in the cavity 61 or axial force otherwise exerted on the plunger 54 by the drive 100. This locking of the syringe 32 to the jacket 31 is preferably achieved, as shown in FIG. 5, by structure at or near the forward wall 57 of the syringe case 50. In accordance with the embodiment of FIG. 15, such structure may include external threads 200 on the forward end of the syringe body 257, which mate with internal threads 201 at the remote end of the jacket 31. With such an embodiment, the syringe 32 is preferably provided with an annular flange 203 around the body 257 at the juncture of the body 257 with the syringe front wall 258. The flange 203 inhibits the flow of leaked fluid into the space between the syringe body 257 and the jacket 31. With such an embodiment, the wall 258 is either thickened, provided with reinforcing such as the ribs 208, or provided with other structure to resist deformation of the wall 258 under the pressure of the fluid within the cavity 61.

Alternatively, a reusable split clip 210 may be employed to secure a continuous flange 203 of such a syringe to a continuous flange 212 at the end of the pressure jacket in the embodiment of FIGS. 16. As a further alternative as shown in FIG. 17, a ring clip 210a having an outer rim 215 and rotatably mounted to the syringe 31, encircles and engages outwardly projecting threads of a disk flange 213 formed at the front end of the jacket 31, as the syringe 32 is twisted onto the jacket 31, to engage the jacket in a manner similar to the threads 85 and 86 in the embodiment of FIGS. 2-12 above.

The invention has been described in the context of its preferred embodiments. It will be appreciated by those skilled in the art that variations and alternatives to the embodiments described may be employed without departing from the principles of the present invention. Accordingly, this patent is not intended to be limited except by the scope of the following claims.

We claim:

1. A disposable replacement syringe for a front loadable injector for injecting liquid into an animal, the disposable syringe comprising:
    a hollow elongated tube having a uniform cross-section exterior surface along substantially its entire length to facilitate sliding contact over substantially its entire length with the interior surface of an injector pressure jacket when inserted therein, said tube having a longitudinal axis, a front end containing a front wall having a discharge outlet therein, and a rear end terminating in a rear peripheral edge defining a plunger drive receiving opening, the tube being significantly outwardly deformable, unless additionally restrained on the outside thereof, when fluid pressurized to angiographic injection pressure is contained within the tube;
    a plunger snugly slidable within said tube and having a rearwardly facing coupling thereon engageable with said plunger drive; and
    front end locking means permanently fixed to and exposed exteriorly of said tube proximate said front end thereof to facilitate locking of said tube against longitudinal movement with respect to the front of an injector pressure jacket when inserted therein.

2. The disposable replacement syringe of claim 1 for an injector for injecting fluid at a predetermined operating pressure, wherein:
    the front wall has pressure restraining structure of sufficient strength to support the front wall when fluid at the predetermined operating pressure is contained within the tube.

3. A disposable replacement syringe for a front loadable injector for injecting liquid into an animal, the disposable syringe comprising:
    a hollow elongated tube having a uniform cross-section exterior surface along substantially its entire length to facilitate sliding contact over substantially its entire length with the interior surface of an injector pressure jacket when inserted therein, said tube having a longitudinal axis, a front end containing a front wall having a discharge outlet therein, and a rear end terminating in a rear peripheral edge defining a plunger drive receiving opening;

a plunger snugly slidable within said tube and having a rearwardly facing coupling thereon engageable with said plunger drive;

front end locking means permanently fixed to and exposed exteriorly of said tube proximate said front end thereof to facilitate locking of said tube against longitudinal movement with respect to the front of an injector pressure jacket when inserted therein; and the locking means including thread means fixed to the syringe proximate the front end of the tube.

4. The disposable replacement syringe of claim 3 wherein:

the thread means includes a plurality of thread sections circumferentially spaced around the tubular body proximate the front end thereof and collectively circumferentially spanning less than the full circumference of the tube.

5. The disposable replacement syringe of claim 3 wherein:

the tube is cylindrical and the thread means is lockable upon less than a full rotation of the tube about the longitudinal axis.

6. A disposable replacement syringe for a front loadable injector for injecting liquid into an animal, the disposable syringe comprising:

a hollow elongated tube having a uniform cross-section exterior surface along substantially its entire length to facilitate sliding contact over substantially its entire length with the interior surface of an injector pressure jacket when inserted therein, said tube having a longitudinal axis, a front end containing a front wall having a discharge outlet therein, and a rear end terminating in a rear peripheral edge defining a plunger drive receiving opening;

a plunger snugly slidable within said tube and having a rearwardly facing coupling thereon engageable with said plunger drive;

front end locking means permanently fixed to and exposed exteriorly of said tube proximate said front end thereof to facilitate locking of said tube against longitudinal movement with respect to the front of an injector pressure jacket when inserted therein; and the locking means including a plurality of internal thread sections collectively spanning less than half of the full circumference of the tube with openings therebetween spanning at least four equally spaced 45° segments of the circumference of the tube.

7. A disposable replacement syringe for a front loadable injector for injecting liquid into an animal, the disposable syringe comprising:

a hollow elongated tube having a uniform cross-section exterior surface along substantially its entire length to facilitate sliding contact over substantially its entire length with the interior surface of an injector pressure jacket when inserted therein, said tube having a longitudinal axis, a front end containing a front wall having a discharge outlet therein, and a rear end terminating in a rear peripheral edge defining a plunger drive receiving opening;

a plunger snugly slidable within said tube and having a rearwardly facing coupling thereon engageable with said plunger drive;

front end locking means permanently fixed to and exposed exteriorly of said tube proximate said front end thereof to facilitate locking of said tube against longitudinal movement with respect to the front of an injector pressure jacket when inserted therein; and the front end locking means including screw threads and wherein said cross-section of said tube exterior surface is configured to facilitate rotation of said tube about its longitudinal axis, when located in the injector pressure jacket with said tube exterior surface in snug sliding contact with said injector pressure jacket interior surface, to enable threaded engagement of said front end locking means with the front of an injector pressure jacket to lock said tube against longitudinal movement with respect to the front of the injector pressure jacket.

8. The syringe of claim 7 wherein the screw threads each span less than the circumference of the front end of the tube so as to enable the threaded engagement upon rotation of less than 360°.

9. The syringe of claim 7 wherein said rear end of said tube includes at least one shoulder to facilitate rotation of said tube about its longitudinal axis from the rear end thereof, when said tube is located in an injector pressure jacket and said shoulder is engaged by a syringe rotating member movable in a circular path parallel to said rear peripheral edge of said tube, to enable said threaded engagement of said front end locking means with the front of an injector pressure jacket to lock said tube against longitudinal movement with respect to the front of said injector pressure jacket.

10. The syringe of claim 9 wherein said discharge outlet has a hose receiver located at a predetermined angular orientation relative to said longitudinal axis of said tube, and wherein said at least one shoulder includes three shoulders unequally spaced about said rear peripheral edge to simultaneously facilitate said rotation of said tube about its longitudinal axis from the rear thereof to lock said front end locking means with the front of an injector pressure jacket and orient said hose receiver at said predetermined angular orientation.

11. The disposable replacement syringe of claim 10 further comprising:

orientation restricting means including three notches, each having one of the shoulders formed by an edge of the notch, the notches being unequally spaced about the peripheral edge at the rear end of the tube.

12. The disposable replacement syringe of claim 9 wherein:

the shoulder is formed by an edge of at least one notch at the in the rear peripheral edge of the tube.

13. The disposable replacement syringe of claim 12 further comprising:

orientation restricting means including a plurality of notches, including the notch, unequally spaced about the rear peripheral edge at the rear end of the tube.

14. The syringe of claim 7 wherein said front end locking means includes a lip extending, at least in part, from the front end of said tube, said lip including contiguous outwardly and rearwardly configured lip sections, with said rearwardly extending lip section being outwardly radially spaced from said exterior surface of said tube, and wherein said screw threads are internal threads formed on said rearwardly extending lip section to facilitate threaded engagement of said front end locking means with external threads provided on the exterior front surface of an injector pressure jacket to lock said syringe against longitudinal movement when said tube is inserted in the injector pressure jacket and rotated about its longitudinal axis.

15. The syringe of claim 14 wherein said outwardly configured lip section extends continuously around the front end of said tube to inhibit entry of fluid from the exterior of said syringe into the interface defined by said internal threads on said front end locking means and said external threads on the exterior front surface of an injector pressure jacket.

16. The syringe of claim 15 wherein the front end locking means is carried by a cap formed separate from said front wall and permanently fixed thereto and disposable therewith, said cap having an outer peripheral margin located radially outwardly of said tube exterior surface configured to define said lip.

17. The disposable replacement syringe of claim 2, wherein:
the locking means is connected at least in part to the pressure restraining structure of the front wall of the syringe.

18. The disposable replacement syringe of claim 17, wherein:
the pressure restraining structure includes a cap fixed to and overlying the front wall of the syringe, the cap having the locking means connected at least in part thereto.

19. The disposable replacement syringe of any of claims 2-18, wherein:
the pressure restraining structure is formed of material separate from that of the front wall of the syringe and is nonremovably fixed to the front wall to be disposable with the syringe.

20. The syringe of claim 1, or 7, or 9, or 10, or 14, or 15, or 16, further comprising injectable fluid medium located within said tube between the front all thereof and said plunger which is dischargeable through said orifice when said plunger is advanced toward said front wall.

21. The disposable replacement syringe of any of claims 11-13 and 17-18, wherein:
the tube is significantly outwardly deformable, unless additionally restrained on the outside thereof, when fluid pressurized to angiographic injection pressure is contained within the tube.

22. A disposable replacement syringe for a front loadable injector for injecting liquid into an animal, the disposable syringe comprising:
a hollow elongated cylindrical tubular body having a fluid holding cavity at least partially contained therein, a front end, and a back end having a circular outer periphery with a plunger drive receiving opening therethrough;
the tubular body having a circular outer cross-section uniform throughout substantially its entire length thereof thereby being capable of slidable contact with a surrounding cylindrical pressure jacket of a similarly sized circular inner cross-section, the outer shape of the body being of a radius at least as great as that of the circular outer periphery of the back end of the tubular body;
the front end of the tubular body having a front wall sealed thereto with a fluid discharge outlet therethrough communicating with the cavity, the front wall including pressure restraining structure providing sufficient strength to support the front wall against deformation when fluid at a predetermined operating pressure is contained within the cavity;
the tubular body having a plunger slidably supported and moveable longitudinally therein between the back end and the front end thereof and forming a fluid tight seal therewith to seal the cavity, the plunger having a rearwardly facing coupling thereon positioned to be engaged by a plunger drive when extended through the opening;
means on the syringe fixed with respect to the body thereof for restricting the angular orientation of the syringe on the injector about a longitudinal axis of the syringe, the orientation restricting means including at least one peripheral notch at the back end of the body, interrupting the periphery and extending over three unequally spaced kay receiving positions, and engageable with cooperating structure of the injector, the at least one notch includes key receiving spaces positioned and configured around the back end of the body to engage the cooperating structure of the injector at only one angular orientation about the axis;
locking means permanently fixed to the syringe proximate the front end of the tubular body and connected at least in part to the pressure restraining structure of the front wall of the syringe for locking the body of the syringe against movement with respect to the injector and for providing at least part of the angular orienting means; and
the locking means including internal threads lying outwardly of the body of the syringe and fixed to the syringe proximate the front end of the tubular body, the threads being lockable upon less than a full rotation of the body and configured and positioned to engage cooperating thread receiving structure on the injector in a limited number of angular orientations about the axis and including a plurality of thread sections circumferentially spaced around the tubular body collectively circumferentially spanning less than half of the full circumference of the tubular body with openings therebetween spanning at least four equally spaced 45° segments of the circumference of the body.

23. The disposable replacement syringe of claim 22 wherein:
the at least one peripheral notch includes three unequally spaced notches, each aligned with a different one of the key receiving positions.

24. The disposable replacement syringe of claim 22 or claim 23 wherein the front wall includes:
a cap separately formed and permanently fixed to the front end of the body and disposable therewith, the locking means being carried at least in part by the cap.

25. The disposable replacement syringe of claim 22 wherein:
the pressure restraining structure is formed of material separate from that of the front wall of the syringe and is non-removably fixed to the front wall to be disposable with the syringe.

26. The disposable replacement syringe of any of claims 22, 23 and 25, wherein:
the tubular body is significantly outwardly deformable, unless additionally restrained on the outside thereof, when fluid pressurized to angiographic injection pressure is contained within the cavity.

27. The disposable replacement syringe of claim 22 wherein:
the front wall of the syringe includes a continuous rim extending outwardly around the front end of the tubular body; and
the locking means is fixed to and projects inwardly from the rim and is spaced outwardly from the tubular body.

28. The disposable replacement syringe of claim 22 wherein:
the front wall has a discharge neck with a discharge orifice therethrough centered on the axis of the syringe;
the discharge neck has a hose connector thereon, the connector including means for receiving a hose at a specific angular relationship to the body about the axis;
the angular orienting means includes means for maintaining the hose receiving means of the connector at the specific angular relationship about the axis when the syringe is mounted in the injector.

* * * * *